United States Patent
Furusawa et al.

(10) Patent No.: US 6,600,861 B2
(45) Date of Patent: Jul. 29, 2003

(54) FIBER BUNDLE AND ENDOSCOPE APPARATUS

(75) Inventors: Koichi Furusawa, Tokyo (JP); Masaru Eguchi, Tokyo (JP); Tetsuya Utsui, Saitama-ken (JP); Tetsuya Nakamura, Saitama-ken (JP); Ryo Ozawa, Tokyo (JP); Shinsuke Okada, Saitama-ken (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 10/180,325

(22) Filed: Jun. 27, 2002

(65) Prior Publication Data

US 2002/0168158 A1 Nov. 14, 2002

Related U.S. Application Data

(62) Division of application No. 09/652,004, filed on Aug. 31, 2000, now Pat. No. 6,456,769.

(30) Foreign Application Priority Data

Sep. 2, 1999 (JP) .............................. 11-248466

(51) Int. Cl.$^7$ ................................. G02B 6/06
(52) U.S. Cl. .................. 385/116; 385/117; 385/118; 385/115
(58) Field of Search ................. 385/115, 116, 385/117, 118, 119, 120

(56) References Cited

U.S. PATENT DOCUMENTS

| 3,902,880 | A | * | 9/1975 | Strack | 385/115 |
| 4,564,261 | A | * | 1/1986 | Kojima et al. | 385/115 |
| 5,321,501 | A | | 6/1994 | Swanson et al. | 356/345 |
| 5,644,642 | A | | 7/1997 | Kirschbaum | 382/102 |
| 6,438,302 | B1 | | 8/2002 | Utsui et al. | 385/117 |
| 6,456,769 | B1 | * | 9/2002 | Furusawa et al. | 385/117 |

FOREIGN PATENT DOCUMENTS

WO 98/38907 9/1998

* cited by examiner

*Primary Examiner*—Phan T. H. Palmer
(74) *Attorney, Agent, or Firm*—Greenblum & Bernstein, P.L.C.

(57) ABSTRACT

A fiber bundle for image transmission includes pluralities of first optical fibers and a plurality of second optical fibers. Both pluralities of optical fibers being tied at their distal ends to form a composite bundle portion. The first optical fibers being tied at their proximal ends to form a first branched bundle portion and the second optical fibers being tied at their proximal ends to form a second branched bundle portion.

9 Claims, 5 Drawing Sheets

FIBER BUNDLE AND ENDOSCOPE APPARATUS

CROSS-REFERENCE TO RELATED APPLICATION

This application is a division of U.S. patent application Ser. No. 09/652,004 now U.S. Pat. No. 6,456,769, filed Aug. 31, 2000, the content of which is herein incorporated in its entirety.

BACKGROUND OF THE INVENTION

1. Field of the Invention

The invention relates to a fiber bundle consisting of a plurality of optical fibers tied in a bundle, and an endoscope apparatus capable of photographing tomographic images of a object inside a living body or the like.

2. Description of the Prior Art

An endoscope system used for observing the interior of a patient's body cavity has an endoscope to be inserted into the patient's body cavity and an external unit connected to this endoscope. The external unit includes a light source section and a processor.

The endoscope has an elongate insertion cube to be inserted to the patient's body cavity. The endoscope also has an illumination optical system, an objective optical system and a CCD. The illumination optical system, connected with the light source section in the external unit, illuminates an object (which is an inner wall of the body cavity) through an illuminating window provided at the distal end of the insertion tube. The objective optical system forms an image of the object through an observing window provided at the distal end of the insertion tube. The CCD is placed near an image-forming plane of the objective optical system, and connected to the processor in the external unit. Through the insertion tube is laid a forceps charnel which is opened at the distal end of the insertion tube. Through the forceps channel, a forceps or various operative instruments are guided to the distal end of the insertion tube from the proximal end thereof.

By using such an endoscope system, the operator can observe the interior of a patient's body cavity. More specifically, the operator inserts the endoscope into the patient's body cavity, and illuminates a inner wall of body cavity through the illumination optical system. Then, the objective optical system forms the image of the inner wall of the body cavity onto a pick-up plane of the CCD surface. The CCD converts this image into image signals, and transmits the same to the processor in the external unit. The processor in the external unit then processes the received image signals of the inner wall of the body cavity to display the picture of the inner wall onto a monitor. In this state, the operator observes the interior of the patient's body cavity, displayed on the monitor.

If finding a location having the possibility of cancer or a tumor through this observation, the operator inserts a forceps or a biopsy needle into the body cavity through the forceps channel of the endoscope so as to excise tissue from the location. Thus excised tissue is objected to pathologic tests, and a diagnosis is given on the basis of the pathologic test results.

According to the conventional endoscope system of the above-described configuration, what is displayed as images is nothing but the surface of the inner wall of the patient's body cavity. Therefore, biopsy is needed in order to know the condition of tissue under the surface of inner wall of the body cavity. In particular, biopsy is absolutely necessary for early detection of cancer, small tumors, and the like. Nevertheless, the pathologic tests on the tissue excised through the biopsy inevitably consume some time, resulting in a problem that the final diagnosis gets behind.

Moreover, with consideration given to the burden on the patient, the biopsy must be limited in area and in the number of times. Accordingly, simply administering pathologic tests not always promises an accurate diagnosis if lesions might also exist outside the operator-designated biopsy location.

SUMMARY OF THE INVENTION

An object of the present invention is to provide an endoscope apparatus which makes it possible to give an accurate diagnosis in a short time, and a fiber bundle which can be used in such endoscope apparatus.

A fiber bundle according to the present invention, having been devised to achieve the foregoing object has a plurality of first optical fibers and a plurality of second optical fibers. These two types of optical fibers are tied at their distal ends to form a composite bundle portion. The first optical fibers are tied at their proximal ends to form a first branched bundle portion. The second optical fibers are tied at their proximal ends to form a second branched bundle portion.

In the composite bundle portion, both the optical fibers may be tied so that respective distal ends of the first optical fibers and respective distal ends of the second optical fibers are alternately arranged into a checkered pattern to form a square close-packed array as a whole. Moreover, in the composite bundle portion, both the optical fibers may be tied so that each of the first optical fibers is surrounded with six of the second optical fibers to form a hexagonal close-packed array as a whole. Furthermore, in the composite bundle portion, both the optical fibers may be tied so that the first optical fibers are juxtaposed to each other and that the second optical fibers are arranged around the first optical fibers in a square close-packed array or hexagonal close-packed array.

In the first branched bundle portion, the first optical fibers may be arranged in either of a hexagonal close-packed array and a square close-packed array. Similarly, in the second branch bundle, the second optical fibers may be arranged in either of a hexagonal close-packed array and a square close-packed array.

An endoscope apparatus according to the present invention, having been devised to achieve the foregoing object has the fiber bundle described above, third optical fibers as many as the first optical fibers in the fiber bundle, an optical coupler, a low-coherent light source, an objective optical system, a reflecting member, an optical path length adjusting mechanism, a photodetector and a control section. The optical coupler optically couples each of the first optical fibers to corresponding one of third optical fibers. The low-coherent light source is arranged on the proximal ends of either the first optical fibers or the third optical fibers, so as to emit low-coherent light to be incident on the optical fibers. The objective optical system is opposed to the distal end of the composite bundle and individually converges low-coherent light beams emitted from the respective distal ends of the first optical fibers in the composite bundle portion and converges the respective low-coherent light beams reflected by an object to be incident on optical fibers as measurement light beams. The reflecting member is opposed to the respective distal ends of the third optical fibers and reflects low-coherent light beams emitted from those respective distal ends to be incident on the third optical fibers as reference light beams. The optical path length adjusting mechanism makes a relative change between the optical path length from the optical coupler to the object through the respective first optical fibers and the optical path length from the optical coupler to the reflecting member through the respective third optical fibers. The photodetector is arranged on the proximal ends of the other of the first optical fibers and the third optical fibers and detects interfered light beams caused by interferences between the measurement light beams and the reference light beams. The control section forms a tomographic image of the object on the basis of a signal detected by the photodetector while the optical path length adjusting mechanism makes the a relative change.

Here, the low-coherent light source may be a superluminescent diode. This low-coherent light source may be arranged on the proximal end of the first optical fibers with the photodetector on the proximal end of the third optical fibers. Alternatively, the low-coherent light source may be arranged on the proximal end of the third optical fibers, with the photodetector on the proximal end of the first optical fibers.

The first optical fibers in the fiber bundle and the third optical fibers maybe a single-mode optical fiber, respectively. The individual first optical fibers in the fiber bundle, the individual third optical fibers, and the optical coupler may have the property of polarization.

The optical path length adjusting mechanism mentioned above may have the structure of moving the reflecting member so as to approach or recede from the distal ends of the third optical fibers to change the optical path length from the optical coupler to the reflecting member through the respective third optical fibers with respect to the optical path length from the optical coupler to the object through the respective first optical fibers. A piezo element may be used as the mechanism for driving the reflecting member. A voice coil motor, a servomotor, or the like may be used instead thereof.

The optical path length adjusting mechanism may change the optical path length from the optical coupler to the object through the first optical fibers with the reflecting member held stationary. The reflecting member may be a reference mirror, a corner cube, or the like.

Furthermore, the endoscope apparatus may be capable of ordinary observations and fluorescence observations through the second optical fibers in the fiber bundle.

The displaying section may include a CRT, a liquid crystal display, a plasma display, or the like.

BRIEF DESCRIPTION OF THE DRAWINGS

The invention will be described below in detail with reference to the accompanying drawings, in which.

DETAILED DESCRIPTION OF THE PREFERRED EMBODIMENTS

Hereinafter, embodiments of the present invention will be described with reference to the accompanying drawings.

First Embodiment

Figure 1:
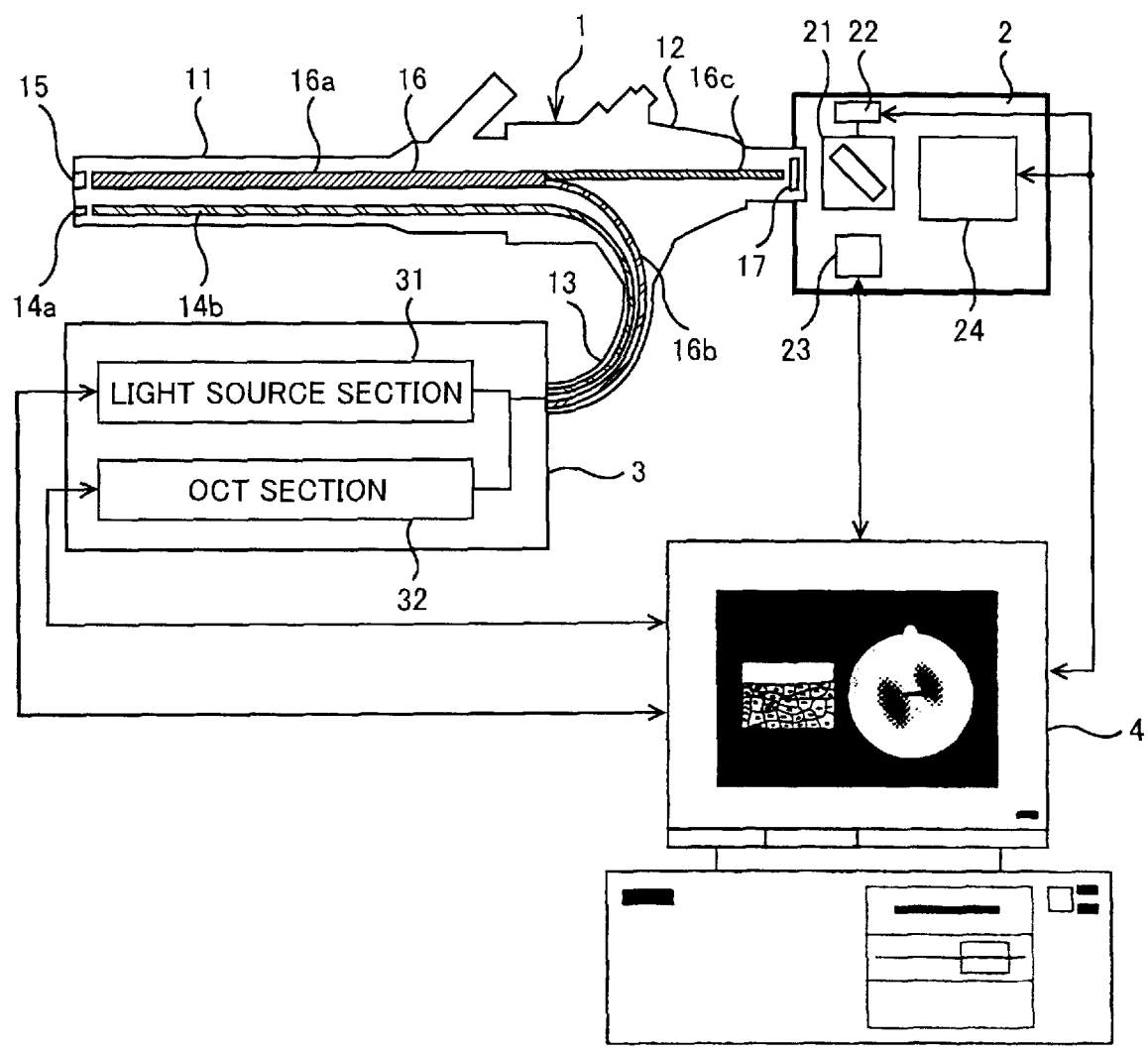
FIG. 1 is a block diagram of the endoscope apparatus according to a first embodiment of the present invention.

An endoscope apparatus according-to the present embodiment has a fiberscope 1, a video camera 2, an external unit 3, and a personal computer (hereinafter, abbreviated as PC) 4. The video camera 2 and the external unit 3 are respectively connected to the fiberscope 1. FIG. 1 is a schematic block diagram of this endoscope apparatus.

Initially, description will be given of the configuration of the fiberscope 1. This fiberscope 1 has an insertion part 11 to be inserted to the interior of a living body, an operation part 12 connected to a proximal end of the insertion part 11, and a connecting tube 13 connected to the operation part 12.

The insertion part 11 is a flexible having an elongate and substantially cylindrical shape. Distal end of the insertion part 11 is sealed with a cylindrical tip member. Through the tip member of the insertion part 11' at least three through holes are formed. One of the through holes is used as a forceps channel. The remaining two are fitted and sealed with a light distribution lens 14a for illumination and the object lens of an objective optical system 15, respectively. The objective optical system 15 includes a cutoff filter for cutting only excitation light which excites self-fluorescence from a living body as well as the objective lens.

The operation part 12 is connected to the proximal end of the insertion part 11 at one end, and is connectable to the video camera 2 at the other end. The operation part 12 contains an imaging optical system 17 adjacent to the end where the video camera 2 is connected. On the surface of this operation part 12 are arranged variety of unillustrated switches for operating and setting the endoscope apparatus. These various switches are connected to the PC 4 through unillustrated signal lines. The connecting tube 13 has flexibility, and is connected to a side face of the operation part 12 at one end and is connectable to the external unit 3 at the other end.

Figure 2:
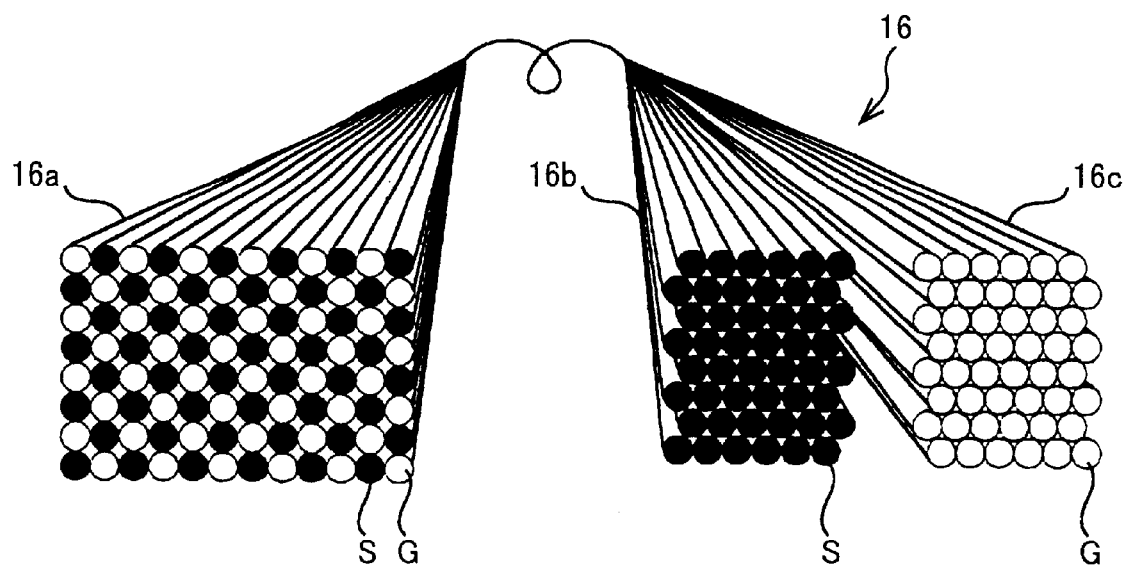
FIG. 2 is a schematic diagram of the fiber bundle according to the first embodiment of the present invention.

A fiber bundle 16 for observation is laid through the insertion part 11, the operation part 12 and the connecting tube 13. This fiber bundle 16 is a single bundle at its distal end, and is branched into two on the proximal side. FIG. 2 is a diagram schematically showing the configuration of the fiber bundle 16. Hereinafter, reference will be also made to this FIG. 2. The fiber bundle 16 includes a plurality (for example, five to ten thousand) of optical fibers S for OCT observation, along with as many optical fibers G for image guide. These two types of optical fibers S and G are identical to each other in diameter. The optical fibers S for OCT observation correspond to the first optical fibers, and the optical fibers G for image guide to the second optical fibers.

At the side of the distal end of the fiber bundle 16, both the optical fibers S and G are tied such that they are arranged in a square close-packed array in cross section. In FIG. 2, for the sake of distinction between the two types of optical fibers S and G, the optical fibers S for OCT observation and the optical fibers G for image guide are schematically represented by black circles and white circles, respectively. Therefore, in FIG. 2, the distal end face of the fiber bundle 16 shows a black and white checkered pattern.

As described above, in the fiber bundle 16, the optical fibers S and G are tied in a square close-packed array from their distal ends to a predetermined length to form a composite bundle portion 16a. The two types of optical fibers S and G are then branched into respective systems on the way. That is, the optical fibers S for OCT observation and the optical fibers G for image guide are separated from each other and independently tied to form an OCT bundle portion 16b and an image guide bundle portion 16c, respectively.

Here, the optical fibers S are tied in a hexagonal close-packed array so that those adjacent to each other in the composite bundle portion 16a adjoin each other even in the branched portion 16c. Besides, the optical fibers G are tied in a hexagonal close-packed array so that those adjacent to each other in the composite bundle portion 12a adjoin each other even in the branched portion 16c. Incidentally, the OCT bundle portion 16b corresponds to the first branched bundle, and the image guide bundle portion 16c to the second branched bundle.

The fiber bundle 16 configured thus is laid through the insertion part 11, the operation part 12 and the connecting tube 13 of the fiberscope 1. More specifically, the fiber bundle 16 is laid through the insertion part 11 and the operation part 12 so that the distal end of its composite bundle portion 16a is opposed to the objective optical system 15 and the proximal end of the image bundle portion 16c is opposed to the imaging optical system 17. Moreover, the OCT bundle portion 16b of the fiber bundle 16 is laid through the operation part 12 and the connecting tube 13 of the fiberscope 1, so that its proximal end is inserted into the external unit 3 in case the connecting tube 13 is connected to the external unit 3.

The fiberscope 1 also contains a light guide fiber bundle (hereinafter, abbreviated as light guide) 14b. This light guide 14b is made by closely binding a plurality of optical fibers for light guide. The light guide 14b is laid through the insertion part 11 with its distal end opposed to the light distribution lens 14a. The light guide 14b is further lead through the operation part 12 and the connecting tube 13 so that its proximal end is introduced into the external unit 3 in case the connecting tube 13 is connected to the external unit 3.

Now, description will be given of the video camera 2. This video camera 2 comprises an optical path selecting mirror 21, an optical path selecting mechanism 22, a ordinary pickup section 23, and a fluorescent pickup section 24. The ordinary pickup section 23 contains a color CCD, and is connected to the PC 4 through signal lines. Meanwhile, the fluorescent pickup 24 is composed of an image intensifier and a CCD, and is connected to the PC 4 through signal lines.

The fluorescent pickup section 24 is arranged on the optical path from the imaging optical system 17 of the fiberscope 1. Moreover, the optical path selecting mirror 21 is arranged on the optical path between the fluorescent pickup section 24 and the imaging optical system 17 of the fiberscope 1. This optical path selecting mirror 21 is coupled to the optical path selecting mechanism 22. The optical path selecting mechanism 22 receives a control signal from the PC 4 through a signal line. In accordant with this control signal, the optical path selecting mechanism 22 switches the position of the optical path selecting mirror 21 between a position out of the optical path of the light emitted from the imaging optical system 17 and a position to cross the optical path at an angle of 45°.

With the distal end of the, insertion part 11 of the fiberscope 1 being opposed to an object, the objective lens 15 of the fiberscope 1 converges the light coming from the object to form an object image on the distal end of the fiber bundle 16. Then, the light incident on each of the optical fibers S and G in the fiber bundle 16 is independently guided through the optical fibers S and G. The light guided through each optical fiber G is emitted from its proximal end, and converged by the imaging optical system 17.

At this time, if the optical path selecting mirror 21 is situated at the position out of the optical path of the light emitted from the imaging optical system 17, the light emitted from the imaging optical system 17 enters the fluorescent pickup section 24. The light having entered the fluorescent pickup section 24 is amplified by the image intensifier, and then re-conversed to form an object image on an image-pickup-plane of the CCD. This CCD converts the object image into image signals and transmits the same to the PC 4, so that an user of this endoscope apparatus may conduct fluorescent observation of the object. Therefore, the state where the optical path selecting mirror 21 is withdrawn from the optical path to introduce the light emitted from the imaging optical system 17 to the fluorescent pickup section 24 will be referred to as fluorescent observation state.

On the other hand, if the optical path selecting mirror 21 is situated at the position to cross the optical path of the light emitted from the imaging optical system 17 at an angle of 45°, the light emitted from the imaging optical system 17 is reflected toward the ordinary pickup section 23. The light reflected by the optical path selecting mirror 21 is converged to form an object image on the image-pickup-plane of the ordinary pickup section 23. The ordinary pickup section 23 converts this object image into image signals, and transmits the same to the PC 4, so that the user may conduct ordinary observation of the object. Therefore, the state where the optical path selecting mirror 21 reflects the light emitted from the imaging optical system 17 to the ordinary pickup section 23 will be referred to as ordinary observation state.

Figure 3:
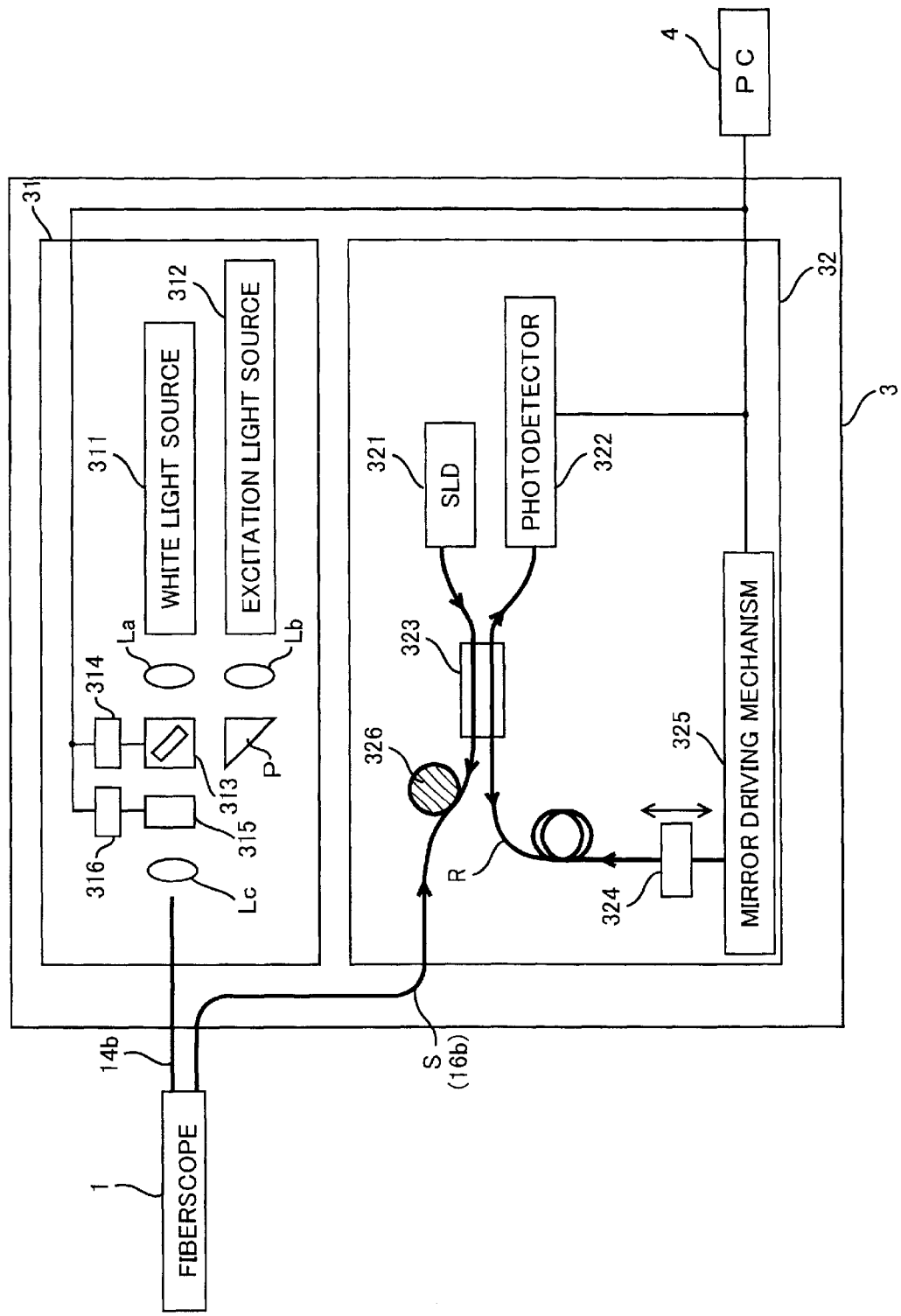
FIG. 3 is a block diagram of the external unit according to the first embodiment of the present invention.

Now, description will be given of the external unit 3. This external unit 3 comprises a light source section 31 and an OCT section 32 both connected to the PC 4. FIG. 3 is a diagram schematically showing the configuration of the external unit 3. Hereinafter, with reference also made to FIG. 3, the light source section 31 and the OCT section 32 of the external unit 3 will be described in order.

The light source section 31 of the external unit 3 has a white light source 311 and an excitation light source 312. The white light source 311 serves as a visible light source for emitting white light (that is, visible light). On the other hand, the excitation light source 312 emits excitation light. The excitation light is ultraviolet to blue light having a wavelength band of approximately 350–400 nm. The excitation light excites living body tissue to show self-fluorescence of approximately 420–600 nm.

On the optical path of the white light emitted from the white light source 311 are arranged in order a collimator lens La, a switching mirror 313, a diaphragm 315 and a condenser lens Lc. The condenser lens Lc is opposed to the proximal end of the light guide 14b. The switching mirror 313 is coupled to a light source switching control mechanism 314. The switching mirror 313 and the light source switching control mechanism 314 function as the light source switching means. More specifically, the light source switching control mechanism 314 puts the switching mirror 313 either in a position out of the optical path of the white light to make the white light pass through or in a position to cross the optical path of the white light at an angle of 45°. The diaphragm 315 is coupled to a diaphragm control mechanism 316. This diaphragm control mechanism 316 can control the diaphragm 315 to adjust the amount of illumination light to be introduced into the fiberscope 1.

By such optical configuration, the white light emitted from the white light source 311 is collimated by the collimator lens La. In this time, if the switching mirror 313 is situated in the position where the white light passes through, the white light proceeds to the diaphragm 315. The white light is adjusted in amount by the diaphragm 315, and then condensed by the condenser lens Lc to enter the light guide 14b.

Meanwhile, on the optical path of the excitation light emitted from the excitation light source 312 are arranged in order a collimator lens Lb and a prism P. The excitation light from the excitation light source 312 is collimated by the collimator lens Lb, and then reflected by the prism P to the switching mirror 313. This switching mirror 313, when situated in the position to cross the white light optical path at an angle of 45°, reflects the excitation light toward the diaphragm 315. The excitation light reflected by the switching mirror 313 is adjusted in amount by the diaphragm 315, and then condensed by the condenser lens Lc to enter the light guide 14b.

In short, the switching mirror 313 takes either of the following two states, one of which is an ordinary observation state where only the white light from the white light source 311 is introduced to the light guide 14b, the other of which is a fluorescent observation state where only the excitation light from the excitation light source 312 is introduced to the light guide 14b. The light source section 31, functions as an illumination optical system together with the light guide 14b and the light distribution lens 14a.

The OCT section 32 of the external unit 3 is a mechanism for obtaining subsurface tomographic images of inner wall of the body cavity wall by utilizing the principles of OCT (optical coherence tomography). The proximal end of the OCT bundle portion 16b of the fiber bundle 16 is laid through this OCT section 32.

This OCT section 32 has a super-luminescent diode (hereinafter, abbreviated as SLD) 321 serving as a low-coherent light source for emitting near-infrared and low-coherent light. The SLD 321 is connected to the PC 4 via an unillustrated drive circuit and signal lines and can emit light which is low-coherent light having a coherence length on the order of e.g. 10–1000 $\mu$m. Each of the optical fibers S in the OCT bundle portion 16b is opposed to the SLD 321 at its proximal end. The SLD 321 can make low-coherent light incident on all the optical fibers S in the OCT bundle portion 16b at the same time.

The OCT section 32 also has a photodetector 322, a plurality of optical fibers R as the third optical fibers for guiding reference light which are as many as the optical fibers S, a plurality of optical couplers 323 for providing optical coupling between each optical fiber S and corresponding optical fiber R, a reference mirror 324, a mirror driving mechanism 325 coupled to the reference mirror 324, and a piezo-modulation element 326.

The photodetector 322 includes a CCD, and is connected to the PC 4 through signal lines. Each of the optical fibers R is placed with its proximal end opposed to the photodetector 322. The photodetector 322 can convert the light beam emitted from each optical fiber R into an electric signal and transmit the same to the PC 4 by every predetermined small region on its pickup plane. The PC 4 detects portions on the pickup plane of the photodetector 322 where light is detected and intensities of electric signals motivated at the portions. Thereby, the PC 4 can recognize the intensity of the light beam emitted from each optical fiber R.

The optical couplers 323 make one-to-one correspondences between the optical fibers S and the optical fibers R, and provide optical coupling between each pair of optical fibers S and R. To be more specific, the optical couplers 323 consist of multi channel optical fiber couplers made by providing fusion splicing between each pair of optical fibers S and R. Incidentally, the optical couplers 323 may be composed of beam splitter prisms instead of the optical fiber couplers.

The optical fibers R are placed with their distal ends opposed to the reference mirror 324. The distal ends of the optical fibers R are fixed in position while the reference mirror 324 is driven by the mirror driving mechanism 325 to make quick reciprocation along the axial direction of the respective optical fibers R. The mirror driving mechanism 325 is connected to the PC 4 through signal lines. The reference mirror 324 corresponds to the reflecting member, and the mirror driving mechanism 325 to the optical path length adjusting mechanism. Here, the optical path length from the optical couplers 323 to the distal ends of the optical fibers S and the optical path length from the optical couplers 323 to the distal ends of the optical fibers R are adjusted to be the same. Additionally, the optical fibers S are wound around the periphery of the piezo-modulation element 326 having cylindrical shape at a predetermined position between the optical couplers 323 and their distal ends. The piezo-modulation element 326 is connected with the PC 4 through an unillustrated drive circuit and signal lines. This piezo-modulation element 326 can repeat radial expansions and contractions at high speed so that the light passing through the optical fibers S wound around itself is modulated in frequency and phase.

In the above-described arrangement, the SLD 321, the photodetector 322, the reference mirror 324, both of the optical fibers S and R, and the optical couplers 323 constitute a Michelson interferometer. Accordingly, with the distal end of the insertion part of the fiberscope 1 opposed to the object (that is, the inner wall of the body cavity), the OCT section 23 can obtain tomographic images of the object. Hereinafter, description will be given of the principles of obtaining such tomographic image. Note that, description will be made on only a single optical fiber S for the sake of simplicity, while the actual OCT section 32 has the multi channel configuration including the same number of channels as the number of optical fibers S as described above.

Low-coherent light emitted from the SLD 321 enters the optical fiber S. The low-coherent light is divided in two by the optical coupler 323 to proceed to the respective distal ends of the optical fibers S and R. The light in the optical fiber S is condensed by the objective optical system 15 and emitted out of the fiberscope 1. The emitted light is reflected by tissue on the surface and of various depths under the surface of the inner wall of the body cavity wall. A part of the reflected light returns into the fiberscope 1. Therefore, it is condensed by the objective optical system 15 and enters the optical fiber S to proceed to the optical coupler 323 as measurement light. Meanwhile, the light halved by the optical coupler 323 to enter the optical fiber R is emitted from the distal end of the fiber R and reflected by the reference mirror 324. The light reflected by the reference mirror 324 reenters the optical fiber R to proceed to the optical coupler 323 as reference light.

The measurement light in the optical fiber S and the reference light in the optical fiber R interfere with each other in the optical coupler 323. It should be noted that the measurement light arrives at the optical coupler 323 with some temporal width because it consists of light beams reflected by various depth of tissue under the inner wall of the body cavity. More specifically, the light beam reflected by the surface of the body cavity wall arrives at the optical coupler 323 earlier, and those reflected by strata deeper than the surface arrive at the optical coupler 323 with some delay. In contrast, the reference light reaches the optical coupler 323 with little temporal width since it is reflected by the reference mirror 324. Accordingly, light beams in the measurement light actually interfere with the reference light are those having traveled over an optical path as long as that from the optical coupler 323 through the optical fiber R to the reference mirror 324. In other words, in the measurement light, only the light beams reflected by a stratum of certain depth beneath the surface of the inner wall of the body cavity causes actual interference with the reference light.

The light beams having made interference in the optical coupler 323 (that is, interfered light) then travels in the optical fiber R to the proximal end, and is detected by the photodetector 322. Accordingly, when the mirror driving mechanism 325 moves the reference mirror 324, the optical path length for the reference light varies to change the depth of the measuring position under the inner wall of the body cavity. The reflected light varies in intensity depending on the conditions of the subsurface tissue of the wall of the body cavity. Thus, a tomographic image is obtained in accordance with the intensity distribution of the light beams reflected by tissue ranging from the surface of the body cavity wall to predetermined depth.

As described above, the photodetector 322 outputs a signal corresponding to the interfered light and low-level noise corresponding to non-interfered light. Lower S/N ratios between the signal and noise can preclude high-accuracy signal extraction. In this view, an optical heterodyne detection method is used to improve the S/N ratio. More specifically, the light passing through the optical fiber S is modulated in frequency and phase by the piezo-modulation element 326. This produces slight deviations in frequency and phase between the measurement light and the reference light, causing beats in the interfered light. Therefore, when the interfered light in this state is received by the photodetector 322, the photodetector 322 outputs a beat signal. Then, the PC 4 can demodulate the beat signal output from the photodetector 322 to extract the signal component with high accuracy.

The OCT section 32 can make such a depthward sweep at one point (that is, measurement point) on the object through its single channel. Since the actual OCT section 32 has the multi channel configuration as described above, the depth-ward sweep can be made over the same number of measurement points as the channels (that is, number of optical fibers S).

As shown in FIG. 2, at the distal end of the composite bundle portion 16a of the fiber bundle 16, the respective end faces of the optical fibers S arranged in a checkered pattern with predetermined intervals therebetween. Therefore, the respective low-coherent light beams emitted from the optical fibers S are condensed by the objective optical system 15 to converge on the object, respectively. This virtually forms measurement points arranged at regular intervals within a predetermined area on a plane substantially parallel to the surface of the object.

Figure 4:
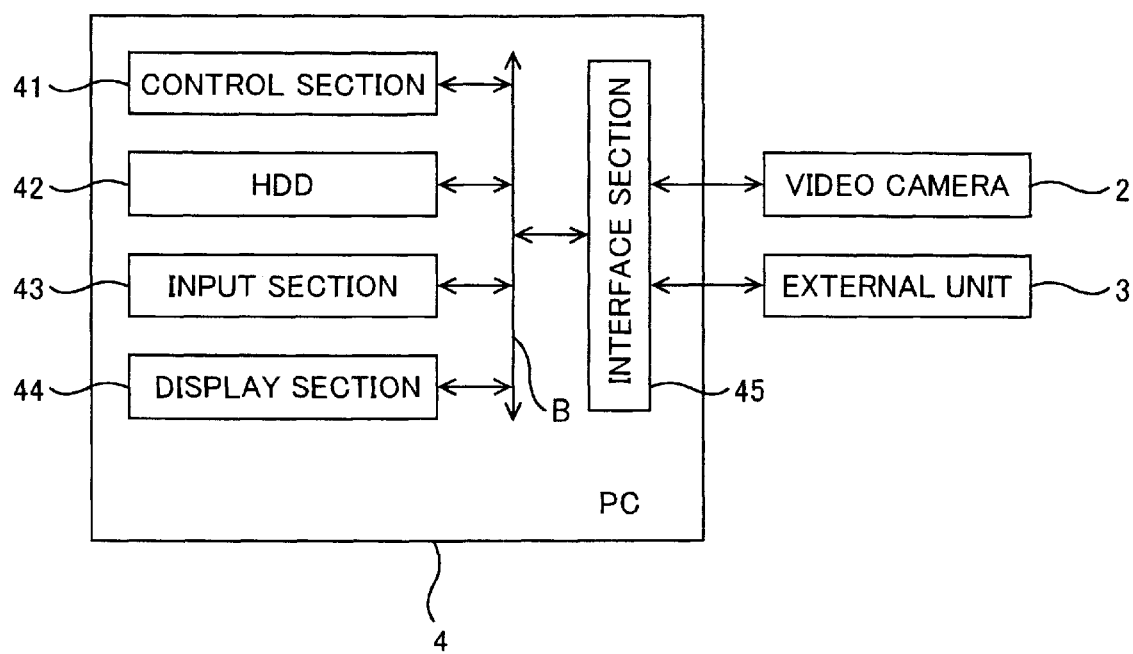
FIG. 4 is a block diagram of the PC according to the first embodiment of the present invention.

Now, description will be given of the PC 4. FIG. 4 is a schematic diagram showing the general configuration of the PC 4. Hereinafter, reference will also be made to this FIG. 4. This PC 4 has a control section 41, a HDD 42, an input section 43, a display section 44, and an interface section 45, which are connected each other via a bus B.

The control section 41 includes an unillustrated CPU and memory. The HDD 42 is capable of data storage, and is preinstalled with programs executed by the control section 41. The input section 43 includes a keyboard interface, along with a keyboard and a mouse connected to the bus B through the keyboard interface, which are unillustrated in the figure. The display section 44 includes a display control circuit having a built-in VRAM (RGB) and a screen such as a color CRT and a color LCD, which are unillustrated in the figure.

The interface section 45 is connected to the optical path selecting mechanism 22, the ordinary pickup section 23 and the fluorescent pickup section 24 in the video camera 2, and the photodetector 322 and the mirror driving mechanism 325 in the external unit 3, through signal lines. Moreover, the interface section 45 has an unillustrated A/D converter, which can convert analog signals output from the ordinary pickup section 23, the fluorescent pickup section 24 and the photodetector 322 into digital signals. The interface section 45 is also connected through the external unit 3 and via unillustrated signal lines to the various switches arranged on the operation part of the fiberscope 1.

The control section 41 can read and execute the programs stored in the HDD 42 to control the input section 42 and the display section 44 and to control the video camera 2 and the external unit 3 through the interface section 45. More specifically, the control section 41 can control the optical path selecting mechanism 22 in the video camera 2 so that the optical path selecting mirror 31 is set to either of the ordinary observation state and the fluorescent observation state. The control section 41 can also control the light source switching control mechanism 314 in the light source section 31 of the external unit 3 so that the switching mirror 313 is set to either of the ordinary observation state and the fluorescent observation state.

When the optical path selecting mirror 21 in the video camera 2 and the switching mirror 313 in the light source section 31 of the external unit 3 are set to the ordinary observation state, the control section 41 can process the signals output from the ordinary pickup section 23 of the video camera 2 to display the resultant as an ordinary image on the display section 44. When the optical path selecting mirror 21 in the video camera 2 and the switching mirror 313 in the light source section 31 of the external unit 3 are set to the fluorescent observation state, the control section 41 can process the signals output from the fluorescent pickup section 24 of the video camera 2 to display the resultant as a fluorescent image on the display section 44.

Moreover, the control section 41 can send timing signals through the interface section 45 to the mirror driving mechanism 325 in the OCT section 32 of the external unit 3 to make the reference mirror 314 reciprocate at a predetermined frequency. Besides, the control section 41 receives and processes the signals output from the photodetector 322 in the OCT section 32 of the external unit 3 to synthesize a three-dimensional image based on the reflection intensity distribution of low-coherent light in a three-dimensional region defined by the rectangular area in the surface of the object and the predetermined depth. Thereafter, on the bases of the three-dimensional image, the control section 41 can generate a tomographic image corresponding to the object's cross section taken along an arbitrary plane and display this tomographic image on the display section 44.

Hereinafter, operation of the endoscope apparatus of the present embodiment, having the above-described configuration will be described. Initially, the operator turns on the main power supply of the endoscope apparatus, so that the power supplies of the fiberscope 1, the video camera 2, the external unit 3, and the PC 4 are respectively turned on. Then, in the light source section 31 of the external unit 3, the white light source 311 and the excitation light source 3112 light up. The optical path selecting mirror 21 in the video camera 2 is initially set to the ordinary observation state.

The switching mirror 313 in the light source section 31 is also initially set to the ordinary observation state. Accordingly, only the white light from the white light source 311 reaches the diaphragm 315 and the condenser lens Lc. The white light condensed by the condenser lens Lc enters the light guide 14b to be emitted through the distal end thereof toward the light distribution lens 14a. The light distribution lens 14a diverges the white light emitted from the distal end of the light guide 14b, and further emits the same out of the fiberscope 1.

Then, the operator inserts the insertion part 11 of the fiberscope 1 into a patient's body cavity such that the distal end of the insertion part 11 is opposed to the inner wall of the body cavity to be observed. Therefore, the white light emitted from the light distribution lens 14a illuminates the body cavity wall. After this, the light reflected by the inner wall of the body cavity is converged on the distal end of the composite bundle portion 16a of the fiber bundle 16 by the objective optical system 15. As a result, the light enters each of the optical fibers G for image guide and each of the optical fibers S for OCT observation in the composite bundle portion 16a. The respective light beams in the optical fibers G are emitted through the proximal end of the image bundle portion 16c, and condensed by the imaging optical system 17 while being introduced into the video camera 2.

The individual light beams having entered the video camera 2 are reflected by the optical path selecting mirror 21 and converged on the image-pickup-plane of the ordinary pickup section 23. Here, the light beams converged on the image-pickup-plane of the ordinary pickup section 23 are arranged in a hexagonal close-packed array on that image-pickup-plane. The ordinary pickup section 23 obtains image signals indicating the intensities of the individual converged light beams, and transmits the same to the PC 4.

The control section 41 of the PC 4 receives the image signals through the interface section 45. The control section 41 then forms an ordinary image of the body cavity wall based on the image signals. More specifically, the control section 41 forms the ordinary image by converting the respective signals corresponding to the light beams converged in a hexagonal close-packed array on the image-pickup-plane of the ordinary pickup section 23 into signals rearranged in a square close-packed array. The control section 41 then displays the formed ordinary image on the screen of the display section 44. In this state, the operator can see the screen of the display section 44 to observe the surface of inner wall of the patient's body cavity displayed as a color image, which is ordinary observation.

when, the operator turns a switch on the operation part 12 of the fiberscope 1 to designate fluorescent observation. The control section 41 in the PC 4 detects the switching, and controls the light source switching control mechanism 314 in the external unit 3 to set the switching mirror 313 to the fluorescent observation state. At the same time, the control section 41 in the PC 4 controls the optical path selecting mechanism 22 to set the optical path selecting mirror 21 to the fluorescent observation state.

After this, the white light from the white light source 311 is cut by the switching mirror 313, and only the excitation light from the excitation light source 312 reaches the diaphragm 315 and the condenser lens Lc. Then, the excitation light condensed by the condenser lens Lc enters the light guide 14b, and is emitted through the distal end of the light guide 14b toward the light distribution lens 14a. The light distribution lens 14a diverges the excitation light emitted from the distal end of the light guide 14b toward the inner wall of the body cavity so that a predetermined area on the inner wall of the body cavity is irradiated with the excitation light.

When objected to the excitation light in an ultraviolet wavelength region, the tissue constituting the inner wall of the body cavity emits self-fluorescence having a wavelength in a green wavelength region different from that of the excitation light. Tissue with a lesion caused by cancer, a tumor or the like shows self-fluorescence weaker than that normal tissue shows. The self-fluorescence is incident on the objective optical system 15 together with the excitation light reflected from the surface of the body cavity wall.

The objective optical system 15 intercepts the excitation light with its cutoff filter to transmit the self-fluorescence, alone. In addition, the objective optical system 15 condenses the self-fluorescence with its objective lens to converge on the distal end of the composite bundle portion 16a of the fiber bundle 16. The converged self-fluorescence enters each of the optical fibers G for image guide and each of the optical fibers S for OCT observation in the composite bundle portion 16a. The individual light beams in the optical fibers G are emitted through the proximal end of the image bundle portion 16c, and introduced into the video camera 2, while being condensed by the imaging optical system 17.

The light beams having entered the video camera 2 are amplified by the image intensifier in the fluorescent pickup section 24, and individually converged on the image-pickup-plane of the fluorescent pickup section 24. Here, the light beams converged on the image-pickup-plane of the fluorescent pickup section 24 are arranged in a hexagonal close-packed array on that image-pickup-plane. The fluorescent pickup section 24 obtains image signals indicating the intensities of the individual light beams converged, and transmits the same to the PC 4.

The control section 41 in the PC 4 receives the image signals through the interface section 45. The control section 41 then forms a fluorescent image of the inner wall of the body cavity based on the image signals. More specifically, the control section 41 forms the fluorescent image by converting the respective image signals corresponding to the light beams converged in a hexagonal close-packed array on the image-pickup-plane of the fluorescent pickup section 24 into signals rearranged in a square close-packed array. The control section 41 then displays the formed fluorescent image on the screen of the display section 44. In this state, the operator can see the screen of the display section 44 to observe the surface of inner wall of the patient's body cavity, which is fluorescent observations. This allows the operator to identify a location showing weaker self-fluorescence than the others as a location that has the high possibility of being a cancerous or tumors lesion.

If a location suspected of being a lesion is identified through such ordinary observation or fluorescent observations the operator makes observation on the tomographic images of that location for diagnosis. Specifically, the operator operates the operation part 12 of the fiberscope 1 to instruct tomographic photographing, so that the control section 41 of the PC 4 detects this instructions and makes the SLD 321 in the OCT section 32 of the external unit 3 emit low-coherent light as well as controls the mirror driving mechanism 325 to start tomographic photographing.

The low-coherent light emitted from the SLD 321 enters the respective proximal ends of the optical fibers S in the OCT bundle portion 16b. The light beams guided by the optical fibers S are respectively divided in two by the optical couplers 323 to travel the optical fibers S for its distal the end as well as the optical fibers R for its distal end.

The individual light beams guided by the optical fibers S are emitted through the respective distal ends of the optical fibers S at the distal end of the composite bundle portion 16a. The light beams are then condensed by the objective optical system 15 and emitted out of the fiberscope 1. The emitted light beams are individually converged so as to be arranged at regular intervals on a predetermined plane generally parallel to the inner wall of the body cavity. The points on which these light beams are converged are the measurement points. The light beams are reflected from tissue of various depths on and near the surface of the inner wall of the body cavity. The reflected light beams enter the objective optical system 15 to be condensed as measurement light beams. The condensed measurement light beams are incident on the respective distal ends of the optical fibers S and G in the composite bundle portion 16a.

Meanwhile, the light beams guided by the optical fibers R for reference are emitted through the respective distal ends of the optical fibers R. The light beams are then reflected by the reference mirror 324 so as to enter the optical fibers R as reference light beams.

Now, the individual measurement light beams guided by the optical fibers S and the reference light beams guided by the optical fibers R interfere with each other in the optical couplers 323, and proceed to the proximal end of the optical fibers R as interfered light beams. The photodetector 322 converts the respective interfered light beams into signals, and outputs the same to the PC 4. The control section 41 of the PC 4 receives the output signals from the photodetector 322 via the interface section 45, and processes the same to obtain the intensities of the measurement light beams at a certain depth in the respective measurement points.

Here, since the reference mirror 324 is reciprocated by the mirror driving mechanism 325, the optical path length from the optical couplers 322 through the respective optical fibers R to this reference mirror 324 sequentially changes. Accordingly, the depthward scanning position on each measurement point also changes sequentially. In addition, the reference mirror 324 is reciprocating at high speed. Therefore, the control section 41 in the PC 4 can obtain the intensity distribution of the measurement light beams over a three-dimensional region ranging from the surface of the body cavity wall to a predetermined depth within a predetermined short period of time. Then, the control section 41 in the PC 4 synthesizes a three-dimensional image concerning the subsurface tissue of inner wall of the body cavity based on the intensity distribution of the measurement light beams.

In fact, the depthward scan at each measurement point is started at a position closer to the fiberscope 1 than the surface of the inner wall of the body cavity, and conducted as far as a position deeper than the predetermined depth to be measured. During the scan, the control section 41 of the PC 4 keeps monitoring the output signal from the photodetector 322 on each channel. Unless the depthward scanning position at a measurement point reaches the surface of the inner wall of the body cavity, the control section 41 detects no signal on the corresponding channel. The control section 41 detects a signal on that channel at the instant when the depthward scanning position reaches the surface of the body cavity wall. Then, the control section 41 makes a zero adjustment with the depth at which a signal is first detected at this measurement point as the surface of the body cavity wall. More specifically, the control section 41 recognizes the depth at which the first signal is detected as the surface of the inner wall of the body cavity wall (depth 0), and directs the measurement onto the signals obtained in the range from that position to a predetermined depth (e.g. 2 mm). Thus, the three-dimensional image is synthesized over the range from the surface of the inner wall of the body cavity to the predetermined depth.

After the three-dimensional image is synthesized, the operator can designate via the input section 43 of the PC 4 a desired plane (cross section) crossing the inner wall of the body cavity for tomographic observations. Upon this plane designation, the control section 41 in the PC 4 generates a tomographic image of the inner wall of the body cavity taken along that plane and displays the image on the display section 44. In this way, once a three-dimensional image is constructed, the operator can make observations of a tomographic image with any desired angle. Incidentally, the control section 41 can also display this tomographic image beside an ordinary image or a fluorescent image on the display section 44.

Through the observations of this tomographic image, the operator can recognize the condition of the tissue under the surface of the inner wall of the body cavity for accurate and speedy diagnosis. This makes it possible for the operator to find early cancer, small tumors, and the like only by the observations through the endoscope apparatus.

Moreover, the accurate and speedy completion of diagnosis allows the operator to give necessary treatments immediately in accordance with the result of the diagnosis. More specifically, it is even possible to lead a forceps, a laser instrument, and/or other operative instruments through the forceps channel laid through the insertion part 11 of the fiberscope 1 to practice various treatments on the scene. This consequently reduces the burden on the patient.

As described above, the endoscope apparatus in the present embodiment uses the fiber bundle 16 consisting of the composite bundle portion 16a, the OCT bundle portion 16b, and the image bundle portion 16c. Therefore, the field of view in ordinary and fluorescence observations coincides with the field of view of OCT tomographic images. As a result, a location on the inner wall of the body cavity, specified in an ordinary image or a fluorescence image corresponds to OCT tomographic images with precision. This means a further improvement in diagnosis accuracy.

In the above description, the OCT bundle portion 16b consists of optical fibers S tied in a hexagonal close-packed array. However, the optical fibers S may be tied in a square close-packed array instead. Moreover, while the image bundle portion 16c has its optical fibers G tied in a hexagonal close-packed array, the optical fibers G may be tied in a square close-packed array instead.

Second Embodiment

The second embodiment of the present invention differs from the first embodiment in the configuration of the fiber bundle 16. Hereinafter, a fiber bundle 116 according to the second embodiment will be described with reference to FIG. 5.

The fiber bundle 116 is composed of a plurality of optical fibers G for image guide and optical fibers S for OCT observation half as many as the optical fibers G. These two types of optical fibers G and S are identical in diameter. The total number of both optical fibers G' and S' is e.g. 10,000–20,000.

Figure 5:
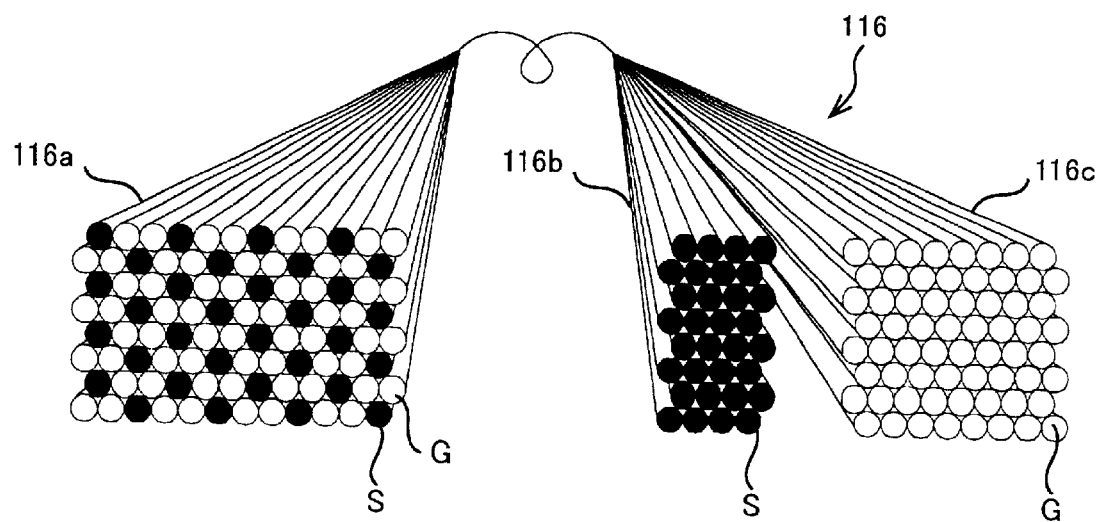
FIG. 5 is a schematic diagram of the fiber bundle according to a second embodiment of the present invention.

In FIG. 5, for the sake of distinction between the two types of optical fibers G and S, the optical fibers G for image guide and the optical fibers S for OCT observation are schematically represented by white circles and black circles, respectively. As shown in this FIG. 5, both the optical fibers G and S in this fiber bundle 116 are tied into a hexagonal close-packed array in cross section at the side of their distal end. More specifically, each of the optical fibers S is arranged so as to be closely surrounded by six of the optical fibers G.

In the fiber bundle 116, both the optical fibers G and S are tied in the hexagonal close-packed array as described above from their distal ends to a predetermined length to form a composite bundle portion 116a. The two types of optical fibers G and S are then branched into respective systems on the way. That is, the optical fibers G for image guide and the optical fibers S for OCT observation are separately bundled to form an image bundle portion 116c and an OCT bundle portion 116b, respectively. The optical fibers G are tied in a hexagonal close-packed array so that those adjacent to each other in the composite bundle portion 116a adjoin each other even in the branched portion 116c. This is similar to the optical fibers S.

As described above, the fiber bundle 116 of the present embodiment has the optical fibers G for image guide arranged more densely than that of the first embodiment. Accordingly, ordinary images and fluorescent images obtained through the optical fibers G are improved in quality.

Third Embodiment

The third embodiment of the present invention differs from the first embodiment only in the configuration of the fiber bundle 16. Hereinafter, a fiber bundle 216 according to the third embodiment will be described with reference to FIG. 6.

Figure 6:
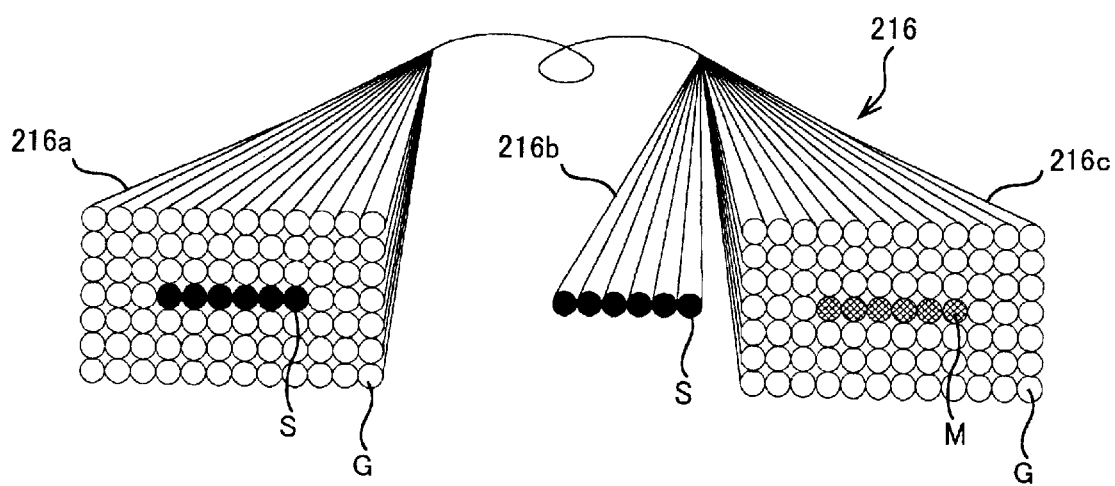
FIG. 6 is a schematic diagram of the fiber bundle according to a third embodiment of the present invention.

The fiber bundle 216 is composed of a plurality (e.g. ten to twenty thousand) of optical fibers G for image guide and a plurality (e.g. several tens to several hundreds) of optical fibers S for OCT observation. In FIG. 6, for the sake of distinction between the optical fibers G and S, the optical fibers G for image guide and the optical fibers S for OCT observation are schematically represented by white circles and black circles, respectively.

The optical fibers S are closely juxtaposed to each other so that the respective centers of their distal ends are aligned in a straight line. Here, FIG. 6 schematically shows only six optical fibers S, whereas the number of optical fibers S juxtaposed actually is on the order of several tens to several hundreds.

The optical fibers G are tied in a square close-packed array so as to surround the juxtaposed optical fibers S to form a composite bundle portion 216a. Incidentally, the optical fibers G may be arranged in a hexagonal close-packed array instead of the square close-packed array. The two types of optical fibers G and S are then branched into respective systems on the way. More specifically, at the side of the proximal end of the fiber bundle 216, the optical fibers S for OCT observation are drawn out and the same number of metal wires M having the same diameter as the optical fibers are filled in place of the optical fibers S. This forms an image bundle portion 216c composed of the optical fibers G for image guide only. Meanwhile, the optical fibers S drawn out are closely juxtaposed to each other so that the respective centers of their proximal ends are aligned in a straight line. This forms an OCT bundle portion 216b.

According to an endoscope apparatus incorporating the fiber bundle 216 of such configuration, OCT tomographic images are obtained from a linear area at the center of the ordinary or fluorescence image view. Therefore, the operator can obtain tomographic images on a location suspected of being a lesion by shifting the distal end of the fiberscope 1 to settle that location at the center of the ordinary or fluorescence image.

In the fiber bundle 216 according to the present embodiment, the number of optical fibers G for image guide is yet greater than that of the second embodiment. This further improves the quality of ordinary images and fluorescence images which are obtained through the optical fibers G. Besides, the closer array of the optical fibers S offers favorable tomographic images.

While the above-described embodiments have dealt with the case where the optical fibers for OCT observation and the optical fibers for image guide are regularly arranged at the distal end of the composite fiber bundle portion, any irregular arrangement may be adopted unless it contains extreme maldistribution.

According to the fiber bundle of the present invention having the above-described configuration, the light having entered through end faces on the composite bundle portion can be branched off into desired states.

Moreover, according to the endoscope apparatus of the present invention, tomographic images can be obtained from a three-dimensional region defined by a predetermined two-dimensional region on a surface of the object and a predetermined depth. Accordingly, if a lesion exists under the surface of the object, the operator can identify the lesion accurately and speedily.

While there has been described what are at present considered to be preferred embodiments of the invention, it will be understood that various modifications may be made thereto, and it is intended that the appended claims cover all such modifications as fall within the true spirit and scope of the invention.

The present disclosure relates to subject matter contained in priority Japanese Patent Application No. HEI 11-248466, filed on Sep. 2, 1999, the contents of which is herein expressly incorporated by reference in its entirety.

We claim:

1. A fiber bundle for image transmission comprising
a plurality of first optical fibers and a plurality of second optical fibers, both said optical fibers being configured at their distal ends to form a composite bundle portion, said first optical fibers being configured at their proximal ends to form a first branched bundle portion, said second optical fibers being configured at their proximal ends to form a second branched bundle portion,
wherein said plurality of second optical fibers are configured to form an image guide fiber bundle, and said plurality of first optical fibers are configured to form an optical fiber probe that optically detects a diseased part and at least some of said plurality of first optical fibers are positioned within said plurality of second optical fibers at said composite bundle portion to detect, through said plurality of first optical fibers, a diseased part of a body corresponding to an image guided through said plurality of second optical fibers.

2. The fiber bundle according to claim 1, wherein
said first optical fibers are juxtaposed to each other and said second optical fibers are arranged around said first optical fibers to form a square close-packed array as a whole in said composite bundle portion.

3. The fiber bundle according to claim 2, wherein said second optical fibers are arranged in a square close-packed array in said second branched bundle portion.

4. The fiber bundle according to claim 1, wherein
said first optical fibers are arranged in a hexagonal close-packed array in said first branched bundle portion.

5. The fiber bundle according to claim 4, wherein
said second optical fibers are arranged in a hexagonal close-packed array in said second branched bundle portion.

6. The fiber bundle according to claim 1, wherein the respective distal ends of said first optical fibers and the respective distal ends of said second optical fibers are alternately arranged into a checkered pattern to form a square close-packed array as a whole in said composite bundle portion.

7. The fiber bundle according to claim 1, wherein said first optical fibers are arranged in a square close-packed array in said first branched bundle portion.

8. The fiber bundle according to claim 1, wherein each of said first optical fibers is surrounded with six of said second optical fibers to form a hexagonal close-packed array as a whole in said composite bundle portion.

9. The fiber bundle according to claim 1, wherein said first optical fibers are juxtaposed to each other and said second optical fibers are arranged around said first optical fibers in said composite bundle portion.

* * * * *